(12) United States Patent
MacDougall et al.

(10) Patent No.: US 11,947,146 B2
(45) Date of Patent: Apr. 2, 2024

(54) CONFIGURABLE OPTICAL APPLICATOR

(71) Applicant: Lumeda inc

(72) Inventors: Trevor MacDougall, South Dartmouth, MA (US); Yi Yang, Storrs, CT (US)

(73) Assignee: Lumeda Inc., Rocky Hill, CT (US)

( * ) Notice: Subject to any disclaimer, the term of this patent is extended or adjusted under 35 U.S.C. 154(b) by 0 days.

(21) Appl. No.: 17/996,721

(22) PCT Filed: Jun. 17, 2022

(86) PCT No.: PCT/US2022/073005
§ 371 (c)(1),
(2) Date: Oct. 20, 2022

(87) PCT Pub. No.: WO2022/266665
PCT Pub. Date: Dec. 22, 2022

(65) Prior Publication Data
US 2023/0408745 A1    Dec. 21, 2023

Related U.S. Application Data

(60) Provisional application No. 63/211,747, filed on Jun. 17, 2021.

(51) Int. Cl.
*F21V 8/00*        (2006.01)
*A61N 5/06*        (2006.01)
*H05B 47/155*      (2020.01)

(52) U.S. Cl.
CPC ............. *G02B 6/001* (2013.01); *A61N 5/062* (2013.01); *H05B 47/155* (2020.01); *A61N 2005/0626* (2013.01); *A61N 2005/063* (2013.01); *A61N 2005/0652* (2013.01)

(58) Field of Classification Search
CPC ...... G02B 6/001; H05B 47/155; A61N 5/062; A61N 5/06–2005/073; A61B 18/20–18/28; H01S 3/00
USPC ..................................... 606/2–19; 607/88–94
See application file for complete search history.

(56) References Cited

U.S. PATENT DOCUMENTS

| | | | |
|---|---|---|---|
| 10,670,779 B1 * | 6/2020 | Veras .................. | G02B 3/0068 |
| 2003/0153825 A1 | 8/2003 | Mooradian | |
| 2007/0282404 A1 * | 12/2007 | Cottrell ............... | A61N 5/0601 |
| | | | 362/572 |
| 2018/0207441 A1 * | 7/2018 | Shafirstein .......... | A61N 5/0616 |
| 2020/0046997 A1 | 2/2020 | Shafirstein | |
| 2020/0384287 A1 | 12/2020 | Hetz | |

* cited by examiner

*Primary Examiner* — Jonathan T Kuo
*Assistant Examiner* — Vynn V Huh
(74) *Attorney, Agent, or Firm* — Matthew J Patterson

(57) ABSTRACT

In some implementations, the device may include an optical diffuser assembly having a plurality of light emitting devices positioned along an axis adjacent to one another and the plurality of light emitting devices are adapted to be selectively addressable to produce an irradiance pattern for each of the plurality of light emitting devices.

8 Claims, 9 Drawing Sheets

CONFIGURABLE OPTICAL APPLICATOR

CROSS REFERENCE TO RELATED APPLICATIONS

This application claims the benefit of U.S. Provisional Application Ser. No. 63/211,747 filed 17 Jun. 2021 as well as Patent Cooperation Treaty Patent Application Serial No. PCT/US22/73005 filed 17 Jun. 2022. The disclosure of the applications above are incorporated herein by reference in their entirety.

BACKGROUND OF THE INVENTION

Field of the Invention

The present disclosure relates to non-ionizing photodynamic therapy.

Description of the Related Art

Light therapy can be used for treatment of conditions in multiple ways. For example, interstitial light therapies involve the delivery of a therapeutic light through a fiber optic device placed proximal to or within a target tumor.

Light therapies can be combined with prior administration of light sensitive medicine (i.e., photosensitizer) that absorbs the therapeutic light and interacts with surrounding tissue constituents (e.g., oxygen) to generate reactive species that can destroy the target tissue. This form of therapy is known as photodynamic therapy ("PDT"). PDT uses light (such as light provided by a laser) to activate a non-toxic drug called a photosensitizer. The process works in three ways: it destroys cancer, shuts down blood vessels that "feed" the tumor, and prompts the immune system to kill cancer cells throughout a human body. It is associated with mild side effects and can be combined with standard chemotherapy and surgery and followed with radiation therapy.

In addition, or alternatively, the energy of the light can be absorbed by blood or external additives (such as metal particles) that convert the light energy into heat, to induce complete destruction of the target tumor tissue.

In typical prior art light therapies it can be important that the entire tumor be illuminated with sufficient dose light in order to administer a successful treatment. It is a deficiency in the prior art that it is difficult to know where and how much light is delivered to the tumor or tissue.

In addition, the efficacy of PDT is determined in part by photodynamic sensitizer availability and radiant exposure. Photofrin and other photodynamic sensitizers can be degraded by light exposure, a process called photobleaching, and this can be measured by loss of photosensitizer characteristic fluorescence. In addition, photobleaching has been shown to provide a prediction of the photodynamic dose delivered. However, quantitative measures of photosensitizer fluorescence can be complicated by changes in tissue optical properties during PDT.

An example of a photodynamic light therapy (PDT) delivery system and method is disclosed in US Patent Application No. 20180207442 wherein the PDT is used for the treatment of a tissue. A plurality of light-transmitting catheters (LTCs) having diffusers mounted at a distal end are provided and placed in the tissue according to a pre-determined treatment plan, wherein an LTC includes a first treatment fiber disposed therethrough, and an LTC includes a dosimetry fiber disposed therethrough. A dose light is provided to the tissue via the light diffusers by way of the first treatment fiber according to the pre-determined treatment plan. The diffusers are manually positioned near the target tissue and the light is monitored using the dosimetry fiber. Light received at the dosimetry fiber is measured using a photodetector in operable communication with the dosimetry fiber. One or more properties of a photosensitizer in the tissue are determined. The treatment plan is modified based on the properties of the photosensitizer, and an updated dose light is provided to the tissue by way of the first treatment fiber according to the modified treatment plan.

Another example of PDT can be found in US Patent Application No. 20180207441 wherein a system and method are disclosed that use a flexible guide (flap) having optical fibers that emit light from a distal end to control the delivery of light dose to a treatment area. This approach overcomes the non-reliable delivery of light dose with a flap that conforms to the target area. Dosimetry control can be improved through the use of a computer controlled motor to move the laser fibers linearly within spheres at a known speed over the target tissue. The spheres position the distal ends of the optical fibers a known distance from the tissue. In some embodiments, treatment time is reduced, and illumination of large surfaces is achieved by using multiple fibers to deliver the light simultaneously.

Referring now to FIG. 1, there is shown an example of a prior art PDT system wherein an optical light diffuser 1 is shown at position 1 within a light transmissible catheter 2 and is in optical communication with optical fiber 3. Although not shown, light transmissible catheter 2 can be positioned within a flexible light flap, such as a Freiburg flap or Harrison Anderson Mick (HAM) applicator and optical fiber 3 can be coupled to a light source such as a laser. The optical light diffuser 1 can comprise a cylindrical light diffuser, and as described herein above the optical light diffuser at position 1 is placed proximate the target tissue and dosimetry light is delivered to the treatment area. In these prior art devices, in order to treat a larger target area optical light diffuser 1 is physically moved to position 2 and another course of dosimetry light is delivered to the treatment area. Using this prior art system, it is known to physically move optical light diffuser 1 to a plurality of positions to provide an irradiance pattern in a manner such that when the process is combined the individual exposures of each position of the optical light diffuser combine to produce the desired "complete target". In addition, prior art optical light diffusers have been used simply as a uniform light source mainly having constant light power emitted over its length. Some prior art optical light diffusers have demonstrated a Gaussian type profile where the light is emitted along the length of the optical light diffuser has not been able to be changed via control of the laser source characteristics.

What is needed is a PDT system that has the ability to be dynamically addressable and spatially configurable over a wider range of target areas.

SUMMARY OF THE INVENTION

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In one general aspect, the optical light delivery system may include an optical diffuser assembly having a plurality of light emitting devices positioned along an axis adjacent to one another, and the plurality of light emitting devices are adapted to be selectively addressable to produce an irradiance pattern for each of the plurality of the light emitting devices. Other embodiments of this aspect include corresponding computer systems, apparatus, and computer programs recorded on one or more computer storage devices, each configured to perform the actions of the methods.

Implementations may include one or more of the following features. An optical light delivery system may include a light source, and at least one optical fiber lead optically coupled to the light source and optically coupled to at least one of the plurality of light emitting devices. The optical light delivery system may include a processor coupled to the light source and adapted to selectively address each of the plurality of light emitting devices. The optical light delivery system where the processor is adapted to produce an irradiance pattern and a dwell time for each of the plurality of the light emitting devices in a manner that when an output of each of the plurality of the light emitting devices combine to produce a desired complete target. The optical light delivery system where the irradiance pattern and the dwell time for each of the plurality of the light emitting devices is in accordance with a treatment plan and where the treatment plan is input to the processor. The optical light delivery system may include a plurality of optical diffuser assemblies positioned substantially parallel along their axes and adjacent to one another. The optical light delivery system may include a flexible light flap adapted to be positioned on or within a human body where in the plurality of optical diffuser assemblies are adapted to be positioned within the flexible light flap. The optical light delivery system where the plurality of light emitting devices may include an optical light diffuser having a first segment and a second segment positioned along the axis adjacent to one another, and the first segment adapted to emit light at a first wavelength and the second segment adapted to emit light at a second wavelength. The optical light delivery system where at least a portion of the first segment is a first thin-film notch filter adapted to block light at the second wavelength and at least a portion of the second segment is a second thin-film notch filter adapted to block light at the first wavelength. The optical light delivery system where at least a portion of the first segment may include a light reflective surface and at least a portion of the second segment may include a light reflective surface. The optical light delivery system may include, a light source, at least one optical fiber lead optically coupled to the light source and optically coupled to the optical light diffuser, a processor adapted to control the light source to selectively address the first segment by emitting light at the first wavelength and to selectively address the second segment by emitting light at the second wavelength. The optical light delivery system may include a light source, a plurality of optical fiber leads optically coupled to the light source and optically coupled to at least one of the plurality of light emitting devices, at least one optical switch having a plurality of optical output channels, where each one of the plurality of optical output channels is in optical communication with a respective one of the plurality of optical fiber leads and a further respective one of the plurality of light emitting devices. The optical light delivery system may include a processor coupled to the at least one optical switch and adapted to control the optical switch to selectively address each of the plurality of light emitting devices. The optical light delivery system where the plurality of light emitting devices may include a plurality of optical light diffusers positioned along the axis adjacent to one another. The optical light delivery system where the plurality of light emitting devices may include a plurality of light deflectors positioned along the axis adjacent to one another. The optical light delivery system may include a plurality of optical diffuser assemblies positioned substantially parallel along their axes and adjacent to one another, and where the at least one optical switch may include a plurality of optical switches and where each one of the plurality of optical switches is optically coupled to a respective one of the plurality of optical diffuser assemblies. Implementations of the described techniques may include hardware, a method or process, or a computer tangible medium.

In one general aspect, method may include providing an optical diffuser assembly having positioning a plurality of light emitting devices along an axis adjacent to one another, selectively addressing the plurality of light emitting devices, producing an irradiance pattern for each of the plurality of the light emitting devices. Other embodiments of this aspect include corresponding computer systems, apparatus, and computer programs recorded on one or more computer storage devices, each configured to perform the actions of the methods.

Implementations may include one or more of the following features. A method may include providing a light source, optically coupling at least one optical fiber lead to the light source, and optically coupling the at least one fiber optic lead to at least one of the plurality of light emitting devices. The method may include electrically coupling a processor to the light source and using the processor to selectively address each of the plurality of light emitting devices. The method may include using the processor to produce an irradiance pattern and a dwell time for each of the plurality of the light emitting devices, combining the irradiance pattern and the dwell time of each of the plurality of the light emitting devices, and determining a desired complete target. The method may include developing a treatment plan using the irradiance pattern and the dwell time for each of the plurality of the light emitting devices and inputting the treatment plan into the processor. The method may include positioning a plurality of optical diffuser assemblies adjacent to one another substantially parallel along their axes. The method may include positioning a flexible light flap on or within a human body and positioning the plurality of optical diffuser assemblies within the flexible light flap. The method where the plurality of light emitting devices may include an optical light diffuser having a first segment and a second segment positioned along the axis adjacent to one another, and the method further may include emitting light at a first wavelength from the first segment, and emitting light at a second wavelength from the second segment. The method may include blocking light at the second wavelength using a first thin-film notch filter on at least a portion of the first segment and blocking light at the first wavelength using a second thin-film notch filter on at least a portion of the second segment. The method where at least a portion of the first segment may include a light reflective surface and at least a portion of the second segment may include a light reflective surface. The method may include, providing a light source, coupling at least one optical fiber lead optically to the light source, coupling the at least one fiber optic lead optically to the optical light diffuser, and controlling the light source using a processor to selectively address the first segment by emitting light at the first wavelength and to selectively address the second segment by emitting light at the second wavelength. The method may include providing a light source, coupling a plurality of optical fiber leads optically to the light source and coupling at least one of the plurality of light emitting devices optically to at least one of the plurality of optical fiber leads, providing at least one optical switch having a plurality of optical output channels, where each one of the plurality of optical output channels is in optical communication with a respective one of the plurality of optical fiber leads and a further respective one of the plurality of light emitting devices. The method may include controlling the at least one optical switch using a processor to selectively address each of the plurality of light emitting devices. The method where the plurality of light emitting devices may include a plurality of optical light diffusers positioned along the axis adjacent to one another. The method where the plurality of light emitting devices may include a plurality of light deflectors positioned along the axis adjacent to one another. The method may include, positioning a plurality of optical diffuser assemblies adjacent to one another substantially parallel along their axes, and where the at least one optical switch may include a plurality of optical switches and where each one of the plurality of optical switches is optically coupled to a respective one of the plurality of optical diffuser assemblies. Implementations of the described techniques may include hardware, a method or process, or a computer tangible medium.

In one general aspect, a device may include one or more processors configured to provide an optical diffuser assembly having position a plurality of light emitting devices along an axis adjacent to one another selectively address the plurality of light emitting devices produce an irradiance pattern for each of the plurality of the light emitting devices. Other embodiments of this aspect include corresponding computer systems, apparatus, and computer programs recorded on one or more computer storage devices, each configured to perform the actions of the methods.

Implementations may include one or more of the following features. The device may include providing a light source optically coupling at least one optical fiber lead to the light source, and optically coupling the at least one fiber optic lead to at least one of the plurality of light emitting devices. The device may include electrically coupling a processor to the light source, and using the processor to selectively address each of the plurality of light emitting devices. The device may include using the processor to produce an irradiance pattern and a dwell time for each of the plurality of the light emitting devices combining the irradiance pattern and the dwell time of each of the plurality of the light emitting devices, and determining a desired complete target. The device may include developing a treatment plan using the irradiance pattern and the dwell time for each of the plurality of the light emitting devices, and inputting the treatment plan into the processor. The device may include positioning a plurality of optical diffuser assemblies adjacent to one another substantially parallel along their axes. The device may include positioning a flexible light flap on or within a human body, and positioning the plurality of optical diffuser assemblies within the flexible light flap. The device where the plurality of light emitting devices may include an optical light diffuser having a first segment and a second segment positioned along the axis adjacent to one another, and the method further may include emitting light at a first wavelength from the first segment, and emitting light at a second wavelength from the second segment. The device may include blocking light at the second wavelength using a first thin-film notch filter on at least a portion of the first segment, and blocking light at the first wavelength using a second thin-film notch filter on at least a portion of the second segment. The device where at least a portion of the first segment may include a light reflective surface and at least a portion of the second segment may include a light reflective surface. The device may include providing a light source coupling at least one optical fiber lead optically to the light source coupling the at least one fiber optic lead optically to the optical light diffuser, and controlling the light source using a processor to selectively address the first segment by emitting light at the first wavelength and to selectively address the second segment by emitting light at the second wavelength. The device may include providing a light source coupling a plurality of optical fiber leads optically to the light source and coupling at least one of the plurality of light emitting devices optically to at least one of the plurality of optical fiber leads providing at least one optical switch having a plurality of optical output channels, where each one of the plurality of optical output channels is in optical communication with a respective one of the plurality of optical fiber leads and a further respective one of the plurality of light emitting devices. The device may include controlling the at least one optical switch using a processor to selectively address each of the plurality of light emitting devices. The device where the plurality of light emitting devices may include a plurality of optical light diffusers positioned along the axis adjacent to one another. The device where the plurality of light emitting devices may include a plurality of light deflectors positioned along the axis adjacent to one another. The device may include positioning a plurality of optical diffuser assemblies adjacent to one another substantially parallel along their axes, and where the at least one optical switch may include a plurality of optical switches and where each one of the plurality of optical switches is optically coupled to a respective one of the plurality of optical diffuser assemblies. Implementations of the described techniques may include hardware, a method or process, or a computer tangible medium.

BRIEF DESCRIPTION OF THE DRAWINGS

So that the manner in which the above-recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following detailed description of the embodiments, reference is made to the accompanying drawings, which form a part hereof, and within which are shown by way of illustration specific embodiments by which the examples described herein may be practiced. It is to be understood that other embodiments may be utilized, and structural changes may be made without departing from the scope of the disclosure.

The current disclosure is related to the dynamic control of a desired irradiance pattern and fluence of light to a broad target area with the ability to an addressable irradiance pattern to optimize the delivery of light to particular locations in an economical and efficient manner for PDT systems.

Figure 2:
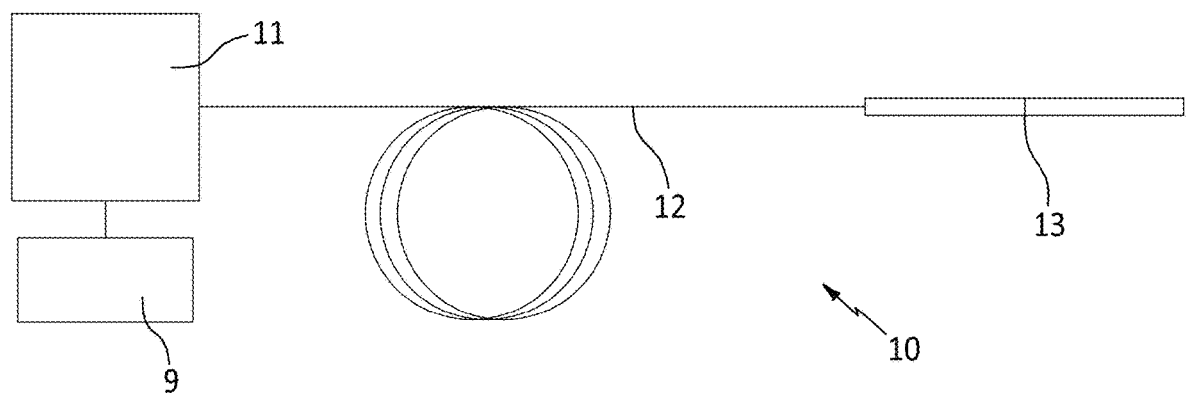
FIG. 2 is a schematic representation of a PDT system having a configurable optical applicator in accordance with the present disclosure.

Referring to FIG. 2, there is shown an embodiment of a configurable optical applicator 10 that includes a processor 9, a light source 11, optical fiber lead 12 and segmented light diffuser 13. Light source 11 can comprise any known light source capable of emitting light at at least two predetermined wavelengths, such as a tunable laser, and launching the emitted light into optical fiber lead 12 wherein the optical fiber lead is comprised of a type of optical fiber, such as a single mode or multi-mode fiber, capable of supporting the propagation of the emitted light from light source 11 to segmented light diffuser 13, also referred to herein as an addressable optical applicator. Processor 9, can comprise a computing device and include other controller type devices as well as volatile and non-volatile memory and wired and wireless communications capabilities.

Figure 3:
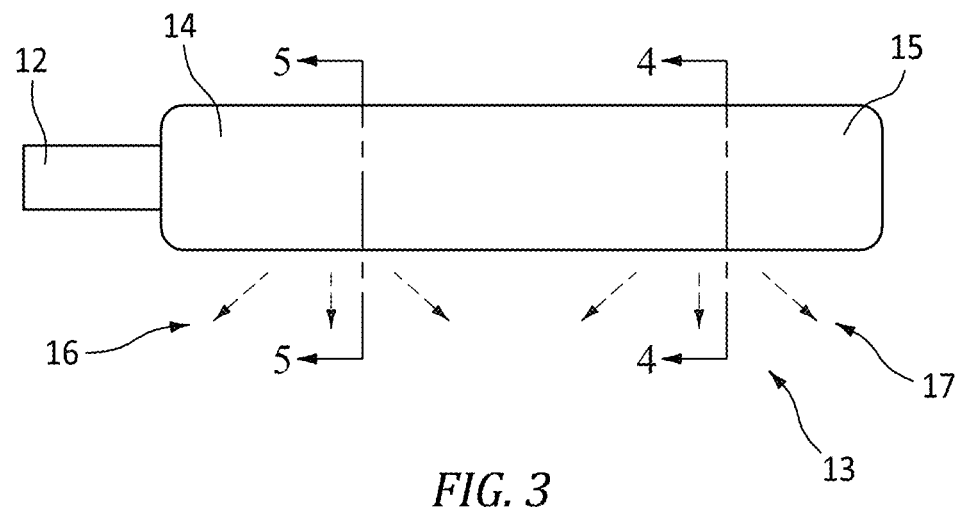
FIG. 3 is an illustration of a configurable optical applicator in accordance with the present disclosure.

Now with additional reference to FIG. 3, segmented light diffuser 13 is an optical light diffuser and can advantageously be a cylindrical light diffuser coupled to optical fiber lead 12 and is shown having two different emitter segments arranged axially along the addressable optical applicator. The addressable optical applicator 13 has a first segment 14 and a second segment 15 wherein the first segment is adapted to emit a first diffuse emission pattern 16 at $\lambda 1$ and the second segment will emit a second diffuse emission pattern 17 at $\lambda 2$. At least a portion first segment 14 and the second segment 15 of addressable optical applicator 13 are coated with a thin-film notch filter having a different reflective center wavelength. In the embodiment shown, and as will be described in more detail hereinafter, first segment 14 of addressable optical applicator 13 is coated with a thin film notch filter adapted to block light at $\lambda 2$ and allow light at $\lambda 1$ to be emitted. Likewise, second segment 15 of addressable optical applicator 13 is coated with a thin film notch filter to block light at $\lambda 1$ and allow light at $\lambda 2$ to be emitted. It should be noted that the filter may effectively block a plurality of wavelengths so long as the filter allows light at the preselected wavelength to be emitted.

Figure 4:
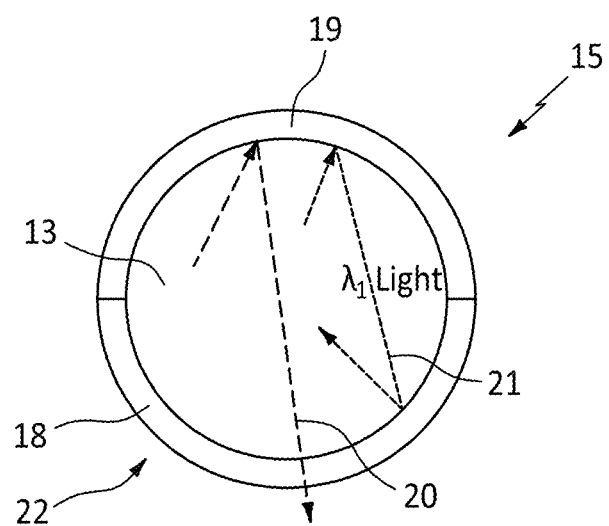
FIG. 4 is a cross sectional illustration of a configurable optical applicator taken along cut line 4-4 of FIG. 3 in accordance with the present disclosure.

Now with further reference to FIG. 4, there is shown a cross sectional view of second segment 15 of addressable optical applicator 13 having thin-film notch filter 18 applied to emitter portion 22 of the exterior of the addressable optical applicator along the axial length of the second segment. In addition, second segment 15 of addressable optical applicator 13 includes an optional substantially fully reflective coating 19, which coating may comprise a gold material, applied to the remainder of the exterior of the addressable optical applicator along the axial length of the second segment. When light source 11 is tuned by processor 9 to produce light having a center wavelength about second wavelength of light 20 at $\lambda 2$ the light will travel through optical fiber lead 12 and first segment 14 and when the produced light enters second segment 15 the light at $\lambda 2$ will be emitted through thin-film notch filter 18 to produce second diffuse emission pattern 17 at $\lambda 2$ through emitter portion 22. It should be noted that the produced light that would otherwise produce a diffuse emission pattern opposite thin-film notch filter 18 becomes incident on reflective coating 19 and is reflected towards emitter portion 22 and inventingly increases the dosimetry light of second diffuse emission pattern 17 at $\lambda 2$ through emitter portion 22. When light source 11 is tuned by processor 9 to produce light having a center wavelength about second wavelength of light 21 at $\lambda 1$ the light will travel through optical fiber lead 12 and first segment 14 and when the produced light enters second segment 15 the light at $\lambda 1$ will be become incident upon, and be reflected by, both thin-film notch filter 18 and reflective coating 19 substantially turning second segment 15 into an "off" condition.

Figure 5:
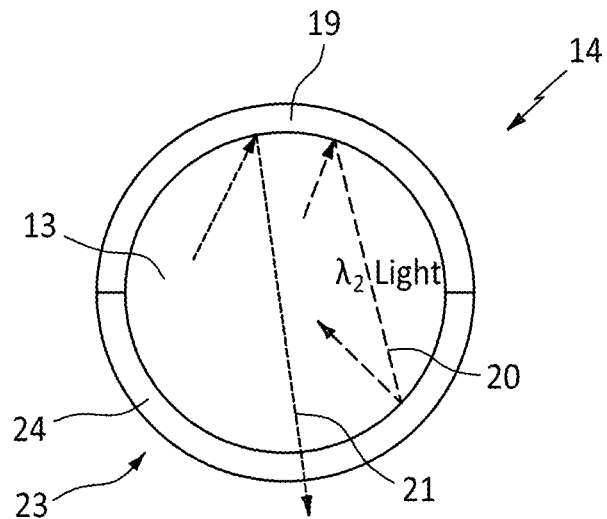
FIG. 5 is a cross sectional illustration of a configurable optical applicator taken along cut line 5-5 of FIG. 3 in accordance with the present disclosure.
Figure 6:
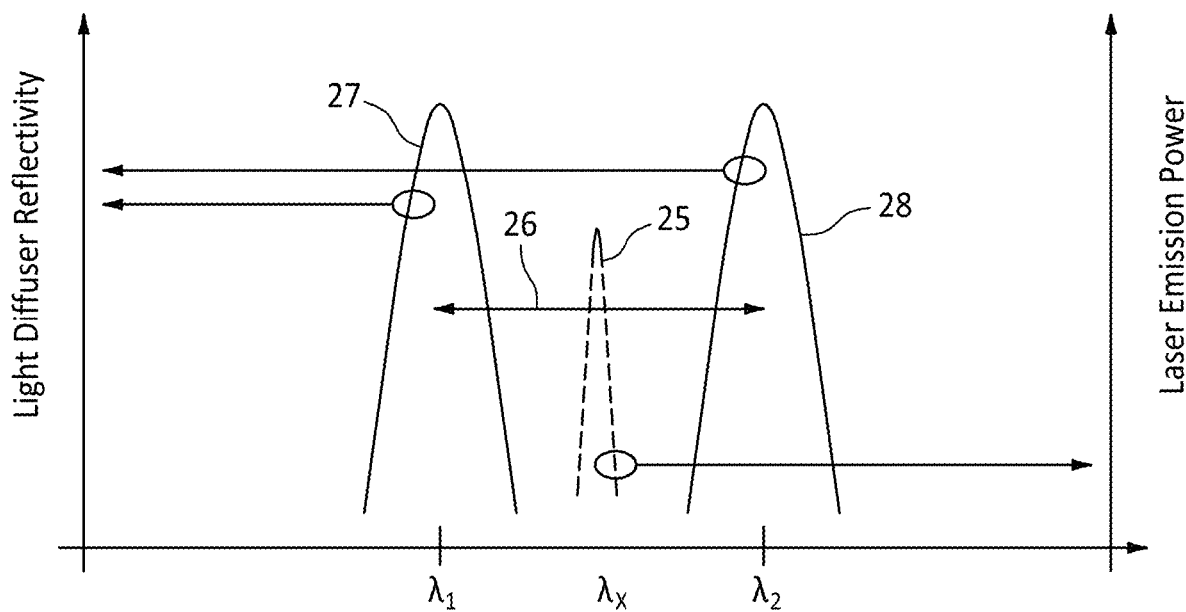
FIG. 6 is a graphical representation of the configurable optical applicator of FIG. 3 in accordance with the present disclosure.

Still referring to FIGS. 2 and 3 and with further reference to FIG. 5, similar to that described herein above with reference to first segment 14 of addressable optical applicator 13, there is shown a cross sectional view of first segment 14 of addressable optical applicator 13 having thin-film notch filter 24 applied to first emitter portion 23 of the exterior of the addressable optical applicator along the axial length of the second segment. In addition, first segment 14 of addressable optical applicator 13 includes an optional substantially fully reflective coating 19, which coating may comprise a gold material, applied to the remainder of the exterior of the addressable optical applicator along the axial length of the first segment. Now with further reference to FIG. 6, wavelength spectrum 25 of light source 11 in terms of emission on the right-hand vertical scale versus wavelength on the horizontal scale. As disclosed above, because light source 11 can comprise a tunable laser its wavelength spectrum can be tuned across a plurality of wavelengths indicated by arrow 26 including wavelengths λ1 and λ2. Also shown in FIG. 6 is the wavelength spectrum 27 of thin-film notch filter 18 depicting its reflectivity on the left-hand vertical scale centered around second wavelength of light 21 at λ1 and wavelength spectrum 28 of thin-film notch filter 24 depicting its reflectivity centered around first wavelength of light 20 at λ2. When light source 11 is tuned to produce light having a center wavelength about first wavelength of light 21 at λ1 the light will travel through optical fiber lead 12 and first segment 14 and when the produced light enters first segment 14 the light at λ1 will be emitted through thin-film notch filter 24 to produce second diffuse emission pattern 16 at λ1 through first emitter portion 23. It should be noted that the produced light that would otherwise produce a diffuse emission pattern opposite thin-film notch filter 24 becomes incident on reflective coating 19 and is reflected towards first emitter portion 23 and inventingly increases the dosimetry light of first diffuse emission pattern 16 at λ1 through first emitter portion 23. When light source 11 is tuned to produce light having a center wavelength about second wavelength of light 20 at λ2 the light will travel through optical fiber lead 12 and when the produced light enters first segment 14 the light at λ2 it will be become incident upon, and be reflected by, both thin-film notch filter 24 and reflective coating 19 substantially turning first segment 14 into an "off" condition.

Figure 1:
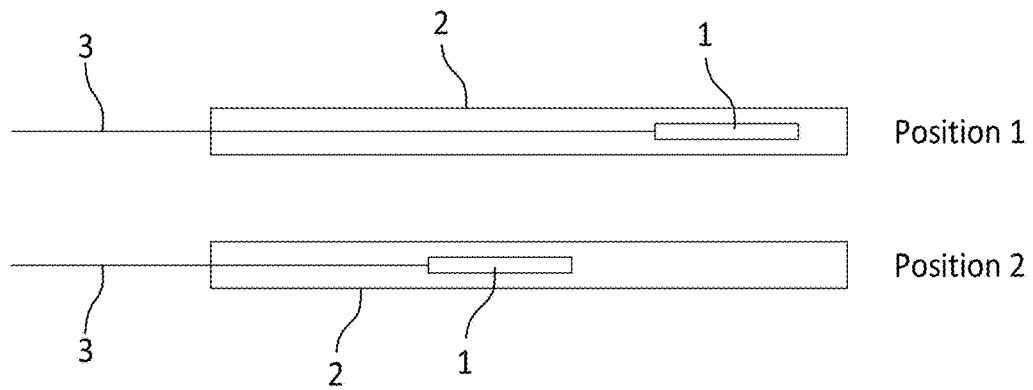
FIG. 1 is an illustration of a prior art optical light diffuser and catheter arrangement.

When configurable optical applicator 10 is used as a PDT treatment system, addressable optical applicator 13 can be disposed into a light transmissive catheter 2 (FIG. 1) and can further be disposed in a Freiburg flap or HAM applicator as disclosed herein above to provide a selectively segmented addressable dosimetry light delivery system having significant advantages over the prior art. In operation, a user can provide processor 9 coupled to light source 11 with a predetermined treatment plan that includes a desired target geometry and dosimetry plan. In accordance with the treatment plan and a preselected photodynamic sensitizer, first wavelength λ1 and second wavelength λ2 are selected based on their efficacy in combination thereof. As an example, addressable optical applicator 13 is disposed over the target area of a patient, for example tissue or organ selected for PDT, and light source 11 is tuned by processor 9 to produce light at first wavelength λ1. As disclosed herein above, an irradiance pattern will be produced over the target area by first diffusion pattern 16 for a predetermined dwell time in accordance with the treatment plan input into processor 9. In the embodiment shown in FIGS. 2-5, addressable optical applicator 13 remains in the initial target position and second segment 15 can subsequently be selectively addressed to provide an optimal irradiance pattern for a second portion of the target area. Light source 11 is tuned by processor 9 to produce light at second wavelength λ2 and as disclosed herein above, an irradiance pattern will be produced over the target area by second diffusion pattern 17 for a predetermined dwell time in accordance with the treatment plan. It should be appreciated by those skilled in the art that configurable optical applicator 10 allows for a larger target area to be treated without having to physically move or translate an optical diffuser. The ability to selectively address first segment 14 and second segment 15 increases the ability to produce a more accurate, timely and configurable irradiance pattern over that known in the prior art. It should further be noted that the example of configurable optical applicator 10 disclosed shows only a single addressable optical applicator 13 having two segments, it is within the scope of the present disclosure that a plurality of segmented light diffusers can be used and that any of the segmented light diffusers can comprise more than two segments producing the obvious benefits by extrapolation of the example disclosed above.

Figure 7:
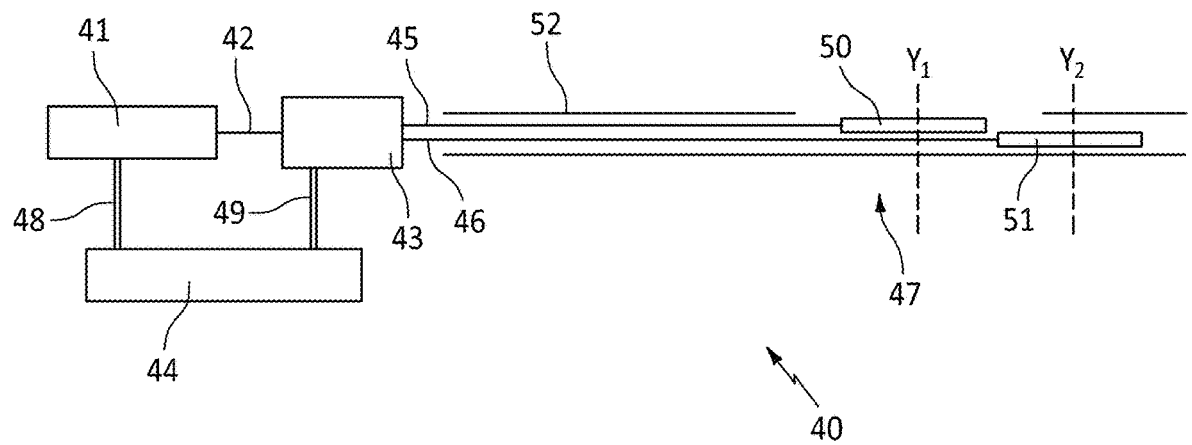
FIG. 7 is schematic representation of a configurable optical applicator in accordance with the present disclosure.

Now with reference to FIG. 7, there is shown an embodiment of a configurable optical applicator 40 that includes a light source 41, optical fiber connector 42, optical switch 43, processor 44, first optical fiber lead 45, second optical fiber lead 46 and segmented light diffuser assembly 47. Light source 41 can comprise any known light source capable of emitting light at a single wavelength or a plurality of predetermined wavelengths, and can comprise a tunable laser, for launching the emitted light into optical switch 43 via optical fiber connector 42 wherein the optical fiber connector is comprised of a type of optical fiber, such as a single mode or multi-mode fiber, capable of supporting the propagation of the emitted light from the light source to the optical switch. Processor 44 is operably connected to light source 41 via light source connector 48 to control operating parameters of the light source including on/off cycles, power levels, wavelengths and other parameters and is further operably connected to optical switch 43 via switch connector 49.

The segmented light diffuser assembly 47 includes first optical light diffuser 50 optically coupled to first optical fiber lead 45, second optical light diffuser 51 optically coupled to second optical fiber lead 46 which are disposed within a housing such as optically transmissive catheter 52. First optical light diffuser 50 and second optical light diffuser 51 are light emitting devices and can comprise cylindrical light diffusers and are positioned axially adjacent to each other within catheter 52 to produce a selectively segmented light diffuser. In some embodiments first optical light diffuser 50 and second optical light diffuser 51 each comprise a single cylindrical light diffuser while in other embodiments they can comprise two different emitter segments arranged axially along the optical light diffuser such as those described herein above with respect to addressable optical applicator 13 (FIG. 3). In an embodiment where first optical light diffuser 50 and second optical light diffuser 51 each comprise a single cylindrical light diffuser, light source 44 can operably produce an emitted light at a single predetermined wavelength. In the embodiment shown, first optical light diffuser 50 and second optical light diffuser 51 are positioned axially adjacent to each other and arranged such that the axial mid-point of the first optical light diffuser is positioned at Y1 and the axial mid-point of the second optical light diffuser is positioned at Y2. The overall axial length of first optical light diffuser 50 and second optical light diffuser 51 can be of any suitable length and in some embodiments comprise relative short axial lengths to provide the attributes of a selectively segmented optical light diffuser as will be disclosed in more detail herein below. Optical switch 43 can comprise a MEMS type optical switch allowing for higher reliability and ability to integrate with automation techniques. Optical switch 43 includes optical output channels and processor 44 controls optical switch 43 to direct emitted light through optical output channels to either first optical fiber lead 45, second optical lead 46 or to both.

Figure 8:
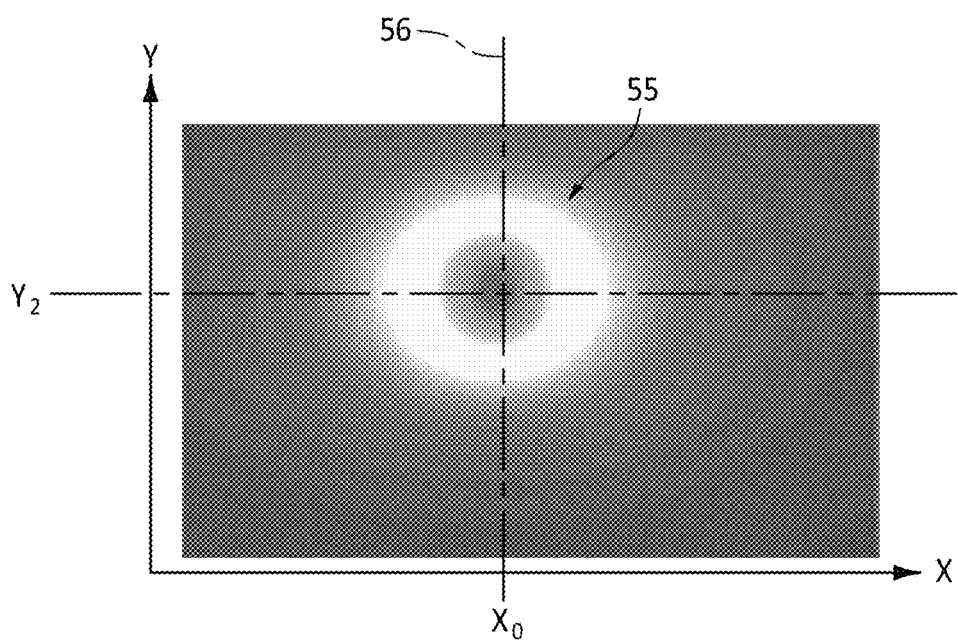
FIG. 8 is an illustration of an irradiance pattern of a configurable optical applicator in accordance with the present disclosure.
Figure 9:
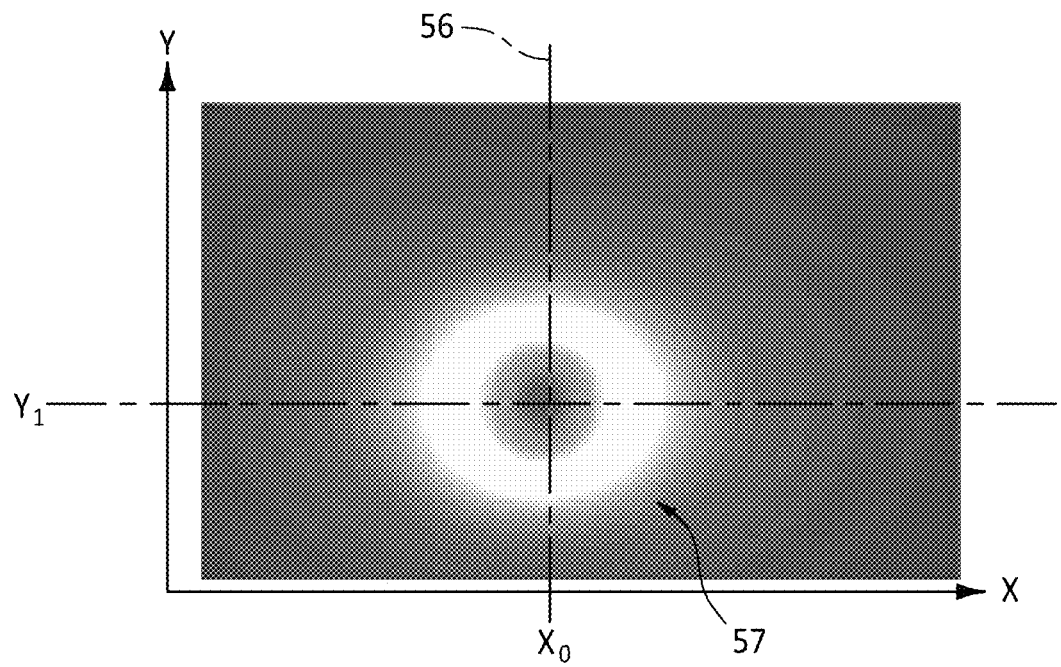
FIG. 9 is an illustration of an irradiance pattern of a configurable optical applicator in accordance with the present disclosure.
Figure 10:
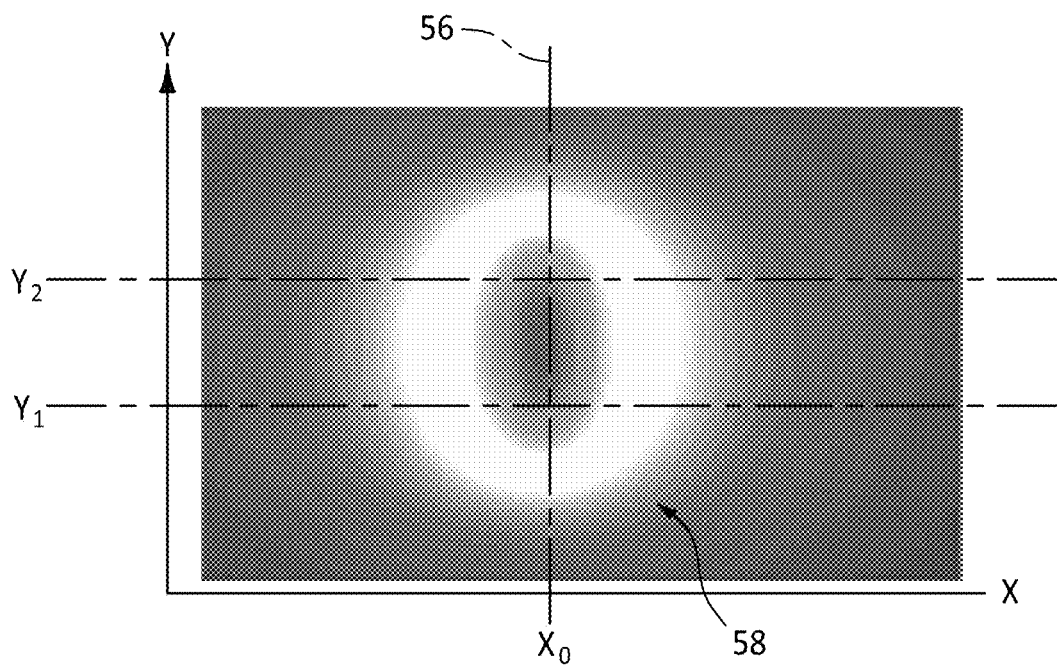
FIG. 10 is an illustration of an irradiance pattern of a configurable optical applicator in accordance with the present disclosure.

In operation, and as configurable optical applicator 40 is used as a PDT treatment system, optical diffuser assembly 47 can further be disposed in a Freiburg flap or HAM applicator as disclosed herein above, or otherwise placed near a target area of a patient, to provide a selectively segmented addressable dosimetry light delivery system having significant advantages over the prior art. A user can provide a processor 44 with a predetermined treatment plan that includes a desired target geometry and dosimetry plan. In accordance with the treatment plan and a preselected photodynamic sensitizer, optical diffuser assembly 47 is disposed over the target area of a patient, for example tissue or organ selected for PDT and processor 44 controls light source 41 and optical switch 43 to produce an optimized irradiance pattern via the optical diffuser assembly. As an example, and with additional reference to FIG. 8, in an embodiment where the treatment plan determined that the irradiance pattern from second optical light diffuser 51 would be effective, processor 44 controls the operating parameters of light source 41 to produce emitted light having at least one frequency and an optical power. Processor 44 further positions optical switch 43 such that the emitted light is directed to second optical fiber lead 46 and into second optical light diffuser 51 to produce second irradiance pattern 55 centered about X0 and Y2, wherein X0 is along the axial length of catheter 52. Processor 44 further controls the dwell time that irradiance pattern 55 is produced in accordance with the treatment plan. With further reference to FIG. 9, in cases where the treatment plan determines that first optical light diffuser 50 would be effective, processor 44 positions optical switch 43 such that the emitted light is directed to first optical fiber lead 45 and into first optical light diffuser 50 to produce second irradiance pattern 57 centered about X0 and Y1, wherein Y1 is a different position from Y2 with respect to the target area and wherein the change in the position of the irradiance pattern is done without having to reposition catheter 52 relative to the target area. Processor 44 further controls the dwell time such that irradiance pattern 57 is produced in accordance with the treatment plan. With still further reference to FIG. 10, in cases where the treatment plan determines that both first optical light diffuser 50 and second optical light diffuser 51 would be effective, processor 44 positions optical switch 43 such that the emitted light is directed to first optical fiber lead 45 and into first optical light diffuser 50 and to second optical fiber lead 46 and into first optical light diffuser 51 to produce second irradiance pattern 58 centered about X0 without having to reposition catheter 52 relative to the target area. Processor 44 controls the dwell time that irradiance pattern 58 is produced in accordance with the treatment plan and can be selectively changed to produce irradiance pattern 55 or irradiance pattern 57 after a predetermined dwell time by repositioning optical switch 43 accordingly. It should be appreciated by those skilled in the art that configurable optical applicator 40 allows for a larger target area to be treated without having to physically move or translate optical diffuser assembly 47. The ability to selectively address first optical light diffuser 50 and second optical light diffuser 51 increases the ability to produce a more accurate, timely and configurable irradiance pattern over that known in the prior art. It should further be noted that the example of configurable optical applicator 40 disclosed shows only a single optical diffuser assembly 47 having two segments, it is within the scope of the present disclosure that a plurality of optical diffuser assemblies can be used and that any of the optical diffuser assemblies can comprise more than two segments producing the obvious benefits by extrapolation of the example disclosed above. It should be further appreciated by those skilled in the art that configurable optical applicator 40 provides a configurable and selectively segmented optical diffuser assembly 47 to provide accurate, stable, fast, finely and selectively adjustable delivery of therapy light to a target area.

As disclosed herein above, and in accordance with a certain embodiment of the present disclosure, first optical light diffuser 50 and second optical light diffuser 51 of optical diffuser assembly 47 can each comprise addressable optical applicator 13 (FIGS. 2, 3) each having a first segment 14 and a second segment 15 for a total of four separate segments. In this embodiment, first optical light diffuser 50 can be configured wherein the first segment is adapted to emit a first diffuse emission pattern at a wavelength of $\lambda 1$ and the second segment is adapted to emit a second diffuse emission pattern at wavelength of $\lambda 2$. In a similar manner, second optical light diffuser 51 can be configured wherein the first segment is adapted to emit a third diffuse emission pattern at a wavelength of $\lambda 3$ and the second segment is adapted to emit a second diffuse emission pattern at wavelength of $\lambda 4$. It should be noted that although the example given provides for four different wavelengths, fewer wavelengths can be used depending on the particular treatment plan without departing from the scope of the present disclosure.

In operation, and as configurable optical applicator 40 is used as a PDT treatment system, optical diffuser assembly 47 can be disposed in a Freiburg flap or HAM applicator as disclosed herein above to provide a selectively segmented addressable dosimetry light delivery system having significant advantages over the prior art. A user can provide a processor 44 with a predetermined treatment plan that includes a desired target geometry and dosimetry plan. In accordance with the treatment plan and a preselected photodynamic sensitizer, optical diffuser assembly 47 is disposed over the target area of a patient, for example tissue or organ selected for PDT and processor 44 controls light source 41 and optical switch 43 to produce an optimized irradiance pattern via the optical diffuser assembly. Also in accordance with the treatment plan and a preselected photodynamic sensitizer, first wavelength $\lambda 1$, second wavelength $\lambda 2$, third wavelength $\lambda 3$ and fourth wavelength $\lambda 4$ are selected based on their efficacy in combination thereof. Processor 44 controls light source 41 to produce an emitted light at first wavelength $\lambda 1$ and positions optical switch 43 to direct the emitted light to optical fiber lead 45 and into first optical light diffuser 50 wherein it will produce an irradiance pattern via the first segment of the first optical light diffuser. As disclosed herein above, processor 44 controls light source 41 to produce the irradiance pattern over the target area by the first segment of first optical light diffuser 50 for a predetermined dwell time in accordance with the treatment plan. In the embodiment shown in FIG. 7, optical diffuser assembly 47 remains in the initial target position and the second segment first optical light diffuser 50 can subsequently be selectively addressed to provide an optimal irradiance pattern for a second portion of the target area. To achieve this condition, processor 44 controls light source 41 to produce an emitted light at second wavelength $\lambda 2$ and positions optical switch 43 to direct the emitted light to optical fiber lead 45 and into first optical light diffuser 50 wherein it will produce an irradiance pattern via the second segment of the first optical light diffuser. Processor 44 further controls light source 41 to produce the irradiance pattern over the target area by the second segment of first optical light diffuser 50 for a predetermined dwell time in accordance with the treatment plan. In cases where a treatment has determined that at least a portion of second optical light diffuser 51 should be used for PDT, processor 44 controls light source 41 to produce an emitted light at third wavelength λ3 and positions optical switch 43 to direct the emitted light to second optical fiber lead 46 and into second optical light diffuser 51 wherein it will produce an irradiance pattern via the first segment of the second optical light diffuser to a third portion of the target area. Processor 44 further controls light source 41 to produce the irradiance pattern over the target area by the first segment of second optical light diffuser 51 for a predetermined dwell time in accordance with the treatment plan. While optical diffuser assembly 47 remains in the initial target position, the second segment second optical light diffuser 51 can subsequently be selectively addressed to provide an optimal irradiance pattern for a fourth portion of the target area. Processor 44 controls light source 41 to produce an emitted light at fourth wavelength λ4 and positions optical switch 43 to direct the emitted light to second optical fiber lead 46 and into second optical light diffuser 51 wherein it will produce an irradiance pattern via the second segment of the second optical light diffuser. Processor 44 further controls light source 41 to produce the irradiance pattern over the target area by the second segment of second optical light diffuser 51 for a predetermined dwell time in accordance with the treatment plan. It should be appreciated by those skilled in the art that configurable optical applicator 40 as just described allows for a larger target area to be treated without having to physically move or translate optical diffuser assembly 47. The ability to selectively address the first segments and second segments of the first optical light diffuser 50 and second optical light diffuser 51 increases the ability to produce a more accurate, timely and configurable irradiance pattern over that known in the prior art. It should further be noted that the example of configurable optical applicator 40 disclosed shows only a single addressable optical applicator having two segments, it is within the scope of the present disclosure that a plurality of SLDs can be used and that any of the SLDs can comprise more than two segments producing the obvious benefits by extrapolation of the example disclosed above.

Figure 11:
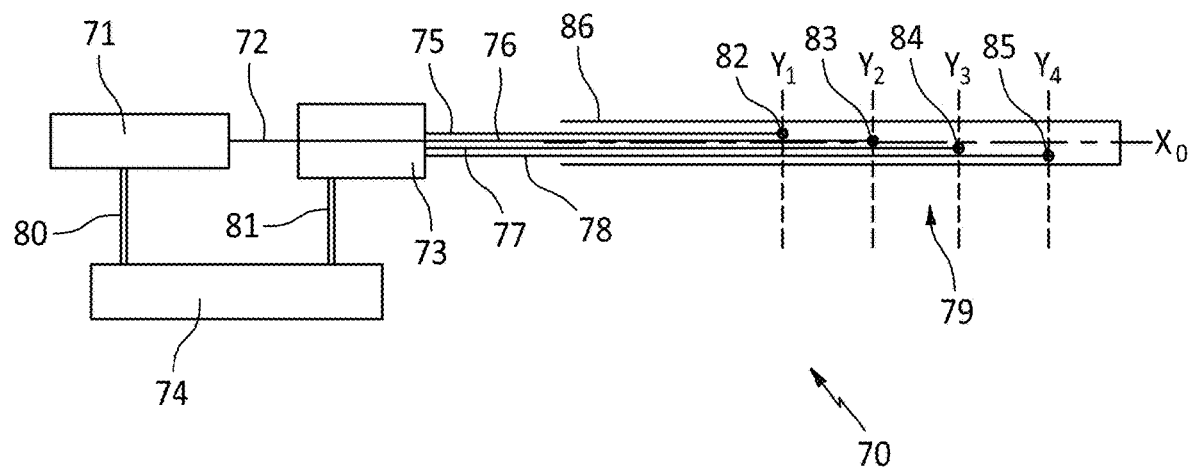
FIG. 11 is schematic representation of a configurable optical applicator in accordance with the present disclosure.

Now with reference to FIG. 11, there is shown an embodiment of a configurable optical applicator 70 that includes a light source 71, optical fiber connector 72, optical switch 73, processor 74, first optical fiber lead 75, second optical fiber lead 76, third optical fiber lead 77, fourth optical fiber lead 78 and segmented light diffuser assembly 79. Light source 71 can comprise any known light source capable of emitting light at a single wavelength or a plurality of predetermined wavelengths, and can comprise a tunable laser, for launching the emitted light into optical switch 73 via optical fiber connector 72 wherein the optical fiber connector is comprised of a type of optical fiber, such as a single mode or multi-mode fiber, capable of supporting the propagation of the emitted light from the light source to the optical switch. Processor 74 is operably connected to light source 71 via light source connector 80 to control operating parameters of the light source including on/off cycles, power levels, wavelengths and other parameters and is further operably connected to optical switch 73 via switch connector 81.

The segmented light diffuser assembly 79 includes first light deflector 82 positioned at Y1 and optically coupled to first optical fiber lead 75, second light deflector 83 positioned at Y2 and optically coupled to second optical fiber lead 76, third light deflector 84 positioned at Y3 and optically coupled to second optical fiber lead 77, and fourth light deflector 85 positioned at Y4 and optically coupled to second optical fiber lead 78 which are disposed within a housing such as optically transmissive catheter 86. First light deflector 82, second light deflector 83, third light deflector 84, and fourth light deflector 85 are positioned axially adjacent to each other within catheter 52 and about the centerline axis X of the catheter to produce a selectively segmented light diffuser as will described in more detail herein after. The size and type of the light deflectors are adapted to produce an irradiance pattern to provide the attributes of a selectively segmented optical light diffuser as will be disclosed in more detail herein below. Optical switch 73 is shown as a 1×4 switch and can comprise a MEMS type optical switch allowing for higher reliability and ability to integrate with automation techniques. Processor 74 controls optical switch 73 to direct emitted light to either first optical fiber lead 75, second optical lead 76, third optical fiber lead 77, fourth optical lead 78, any combination thereof or all.

Figure 12:
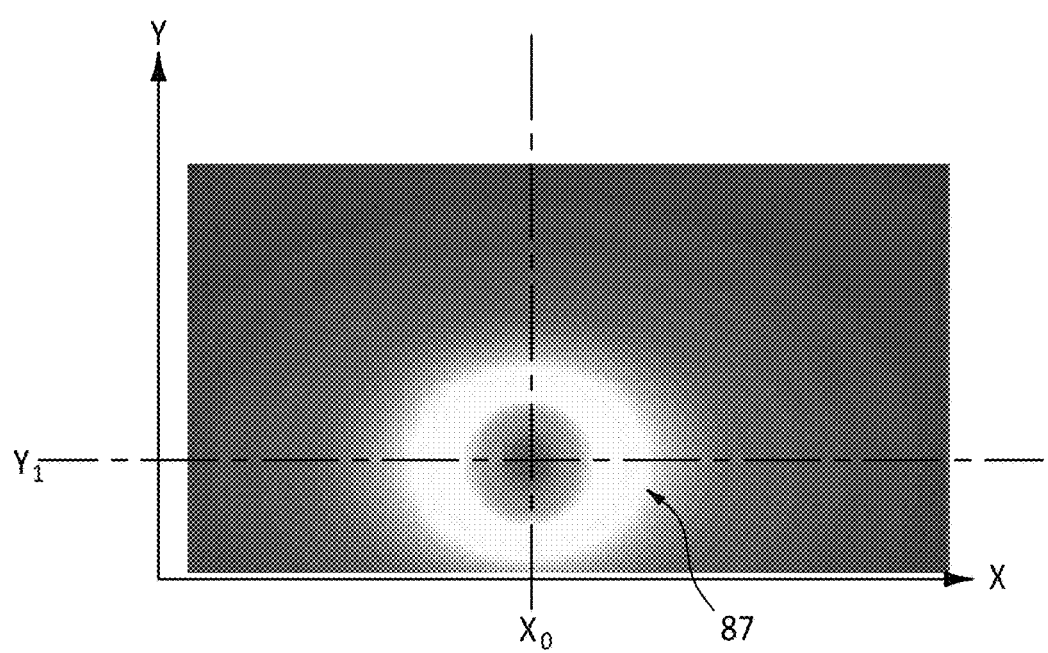
FIG. 12 is an illustration of an irradiance pattern of a configurable optical applicator in accordance with the present disclosure.
Figure 13:
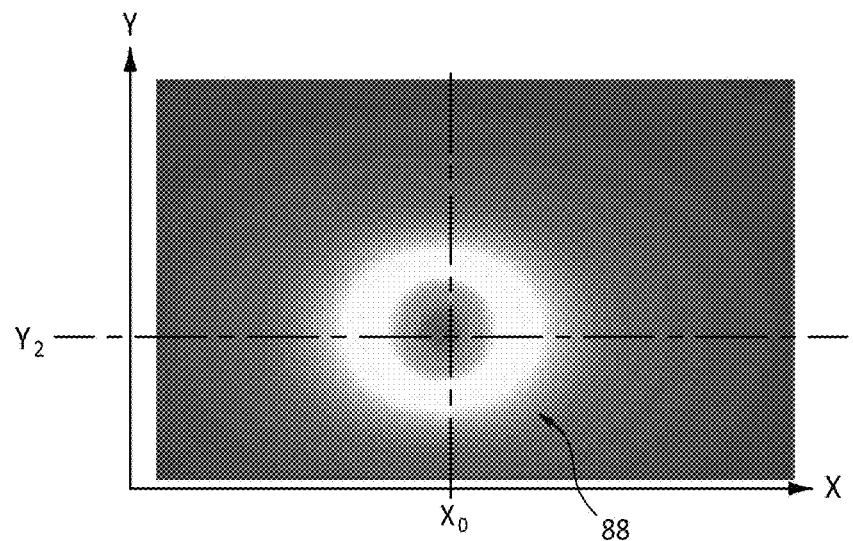
FIG. 13 is an illustration of an irradiance pattern of a configurable optical applicator in accordance with the present disclosure.
Figure 14:
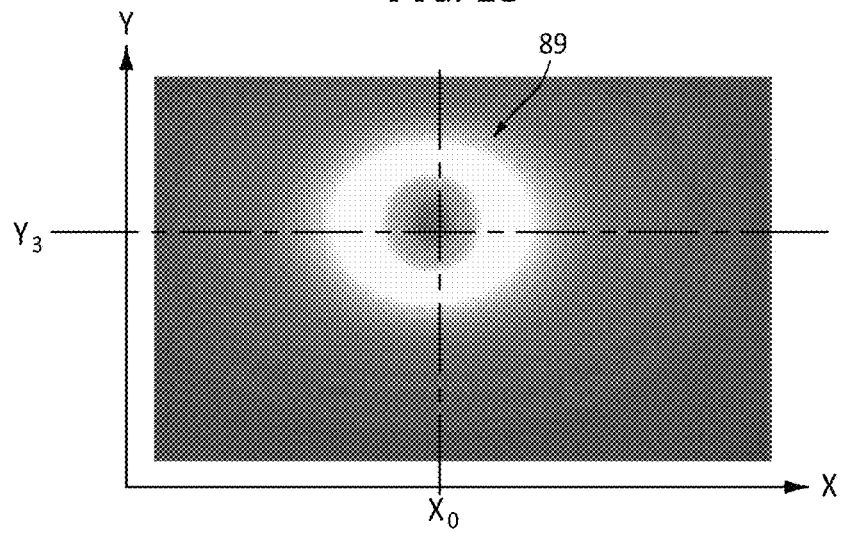
FIG. 14 is an illustration of an irradiance pattern of a configurable optical applicator in accordance with the present disclosure.
Figure 15:
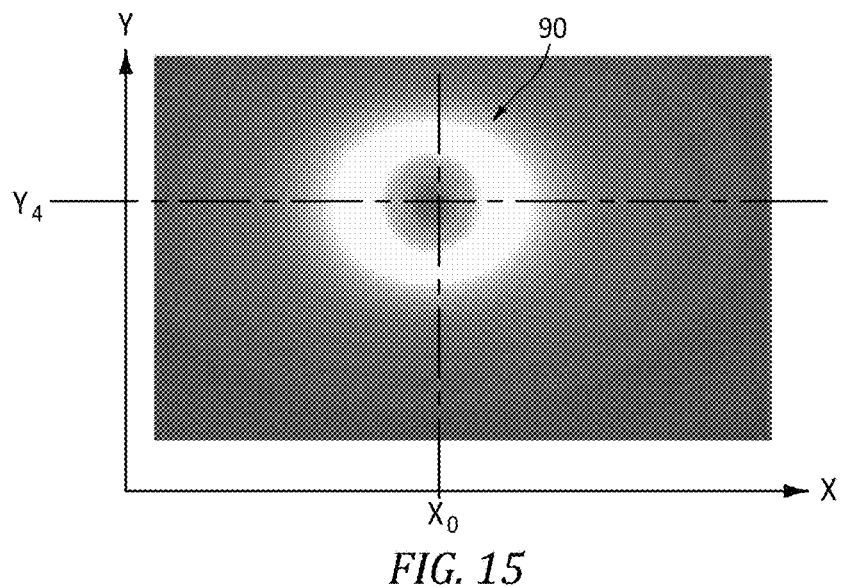
FIG. 15 is an illustration of an irradiance pattern of a configurable optical applicator in accordance with the present disclosure.

In operation, and as configurable optical applicator 70 is used as a PDT treatment system, optical diffuser assembly 79 can further be disposed in a Freiburg flap or HAM application as disclosed herein above, or otherwise placed near a target area of a patient, to provide a selectively segmented addressable dosimetry light delivery system having significant advantages over the prior art. A user can provide processor 74 with a predetermined treatment plan that includes a desired target geometry and dosimetry plan. In accordance with the treatment plan and a preselected photodynamic sensitizer, optical diffuser assembly 79 is disposed over the target area of a patient, for example tissue or organ selected for PDT and processor 74 controls light source 71 and optical switch 73 to produce an optimized irradiance pattern via the optical diffuser assembly. As an example, and with additional reference to FIG. 12, in an embodiment where the treatment plan determined that the irradiance pattern from first light deflector 82 would be effective, processor 74 controls the operating parameters of light source 71 to produce emitted light of a predetermined frequency and optical power. Processor 74 further positions optical switch 73 such that the emitted light is directed to first optical fiber lead 75 and into first light deflector 82 to produce first irradiance pattern 87 centered about X0 and Y1, wherein X0 is along the axial length of catheter 86. Processor 74 further controls the dwell time that irradiance pattern 55 is produced in accordance with the treatment plan. With further reference to FIG. 13, in cases where the treatment plan determines that second light deflector 83 would be effective, processor 74 positions optical switch 73 such that the emitted light is directed to second optical fiber lead 76 and into second light deflector 83 to produce second irradiance pattern 88 centered about X0 and Y2, wherein Y1 is a different position from Y2 with respect to the target area and wherein the change in the position of the irradiance pattern is done without having to reposition catheter 86 relative to the target area. Processor 74 further controls the dwell time such that irradiance pattern 88 is produced in accordance with the treatment plan. Now with further reference to FIG. 14, in cases where the treatment plan determines that third light deflector 84 would be effective, processor 74 positions optical switch 73 such that the emitted light is directed to third optical fiber lead 77 and into third light deflector 84 to produce third irradiance pattern 89 centered about X0 and Y3, wherein Y3 is a different position from Y2 and Y1 with respect to the target area and wherein the change in the position of the irradiance pattern is done without having to reposition catheter 86 relative to the target area. Processor 74 further controls the dwell time such that irradiance pattern 89 is produced in accordance with the treatment plan. Now with still further reference to FIG. 15, in cases where the treatment plan determines that fourth light deflector 88 would be effective, processor 74 positions optical switch 73 such that the emitted light is directed to fourth optical fiber lead 78 and into fourth light deflector 84 to produce third irradiance pattern 90 centered about X0 and Y4, wherein Y4 is a different position from Y3, Y2 and Y1 with respect to the target area and wherein the change in the position of the irradiance pattern is done without having to reposition catheter 86 relative to the target area. Processor 74 further controls the dwell time such that irradiance pattern 90 is produced in accordance with the treatment plan.

Figure 16:
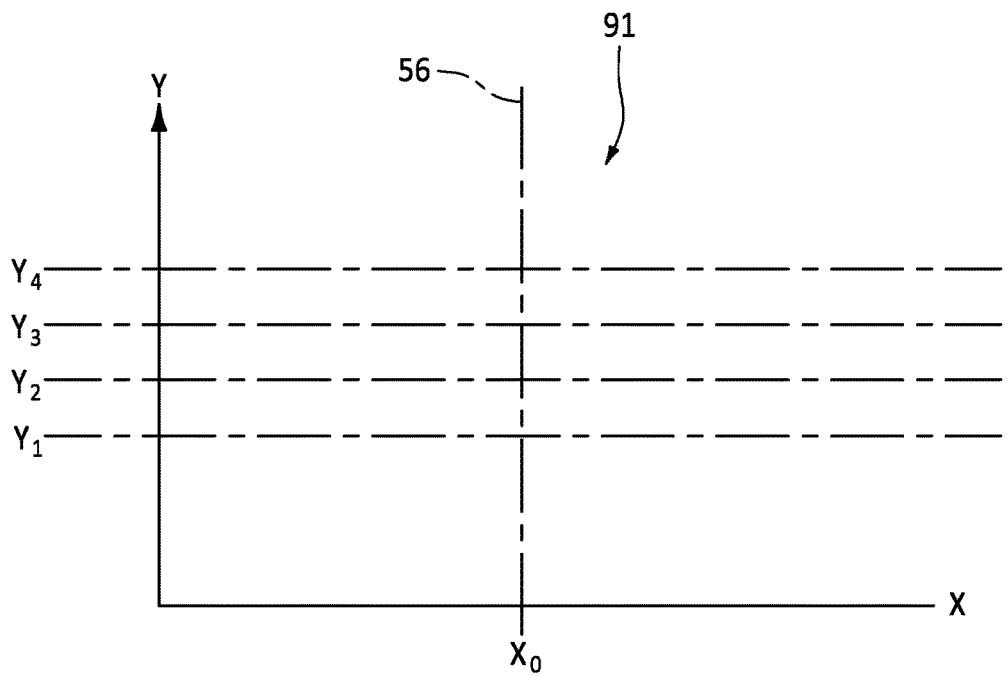
FIG. 16 is an illustration of an irradiance pattern of a configurable optical applicator in accordance with the present disclosure.

With still further reference to FIG. 16, in cases where the treatment plan determines that all of the light deflectors 82-85 would be effective, processor 74 positions optical switch 73 such that the emitted light is directed to all of the optical fiber leads 75-78 and into the light deflectors to produce, for example, a desired complete target, fifth irradiance pattern 91 centered about X0 without having to reposition catheter 86 relative to the target area. Processor 74 controls the dwell time that irradiance pattern 91 is produced in accordance with the treatment plan and can be selectively changed to produce any of the irradiance patterns 87-91 after a predetermined dwell time by repositioning optical switch 73 accordingly. Although described using only five different irradiance patterns, configurable optical applicator 70 is capable of producing 2⁴ or 16 unique irradiance patterns. It should be appreciated by those skilled in the art that configurable optical applicator 70 allows for a larger target area to be treated without having to physically move or translate optical diffuser assembly 79. The ability to selectively individually address light deflectors 82-85 increases the ability to produce a more accurate, timely and configurable irradiance pattern over that known in the prior art. It should further be noted that the example of configurable optical applicator 70 disclosed shows only a single optical diffuser assembly 79 having four light deflectors or segments, it is within the scope of the present disclosure that the optical diffuser assemblies can comprise fewer or more than four segments producing the obvious benefits by extrapolation of the example disclosed above.

Figure 17:
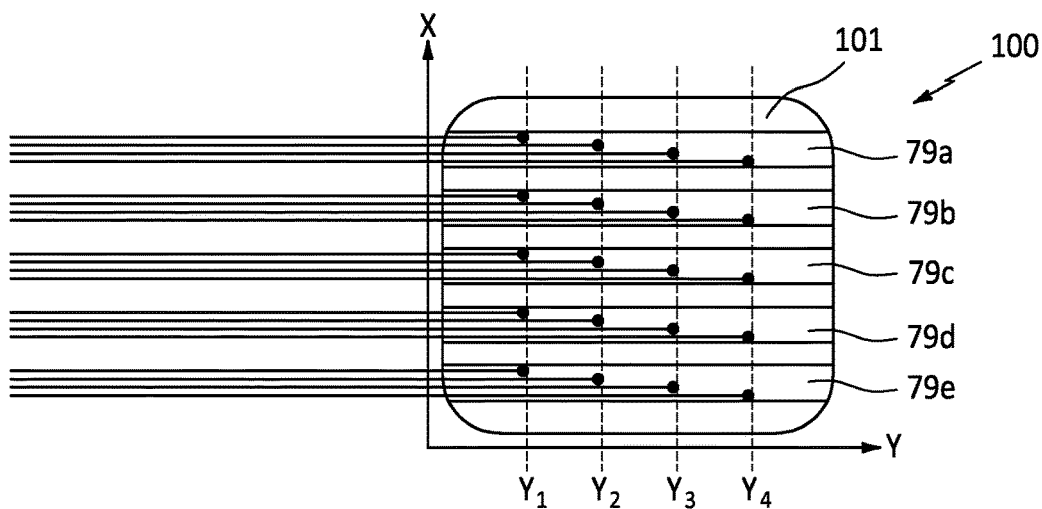
FIG. 17 is schematic representation of a configurable optical applicator in accordance with the present disclosure.

With reference to FIG. 17, there is shown an embodiment of configurable optical applicator 100 which includes a plurality of optical diffuser assemblies 79*a*, 79*b*, 79*c* 79*d* and 79*e*. In the embodiment shown optical diffuser assemblies 79*a*-79*e* are similar to optical diffuser assembly 79 (FIG. 11) having light deflectors 82-85 disposed within a catheter 86 and optically coupled to optical fiber leads 75-78. configurable optical applicator 100 also includes an optically transmissive and flexible carrier 101 that can comprise a Freiburg flap or HAM applicator within which optical diffuser assemblies 79*a*, 79*b*, 79*c* 79*d* and 79*e* are positioned parallel to each other along their axes X0 (FIG. 11) and fixedly positioned relative to the X-Y axes. The optical fiber leads 75-78 of optical diffuser assemblies 79*a*, 79*b*, 79*c* 79*d* and 79*e* can variously be optically connected to light source 71 in any suitable manner including via optical couplers (not shown) connected to the appropriate switch positions of optical switch 73. As an alternative, a plurality of optical switches couple to a single light source or multiple light sources can be optically connected to each of the optical diffuser assemblies 79*a*, 79*b*, 79*c* 79*d* and 79*e* and controlled by processor 74 in the manner disclosed herein above. configurable optical applicator 100 can be controlled by processor 74 to produce irradiance patterns 87-91 for each of the optical diffuser assemblies 79*a*, 79*b*, 79*c* 79*d* and 79*e*. As a demonstration of the ability of configurable optical applicator 100 to provide accurate, stable, fast, finely and selectively adjustable delivery of therapy light to a target area, the possible number of unique irradiance patterns is 2²⁰ or 1,048,576. As should be appreciated by those skilled in the art, selectively configurable PDT systems and methods for their use as disclosed herein provide numerous benefits. The disclosed embodiments allow for the selectively configurable and power level control of the output a plurality of light emitting devices for PDT.

Figure 18:
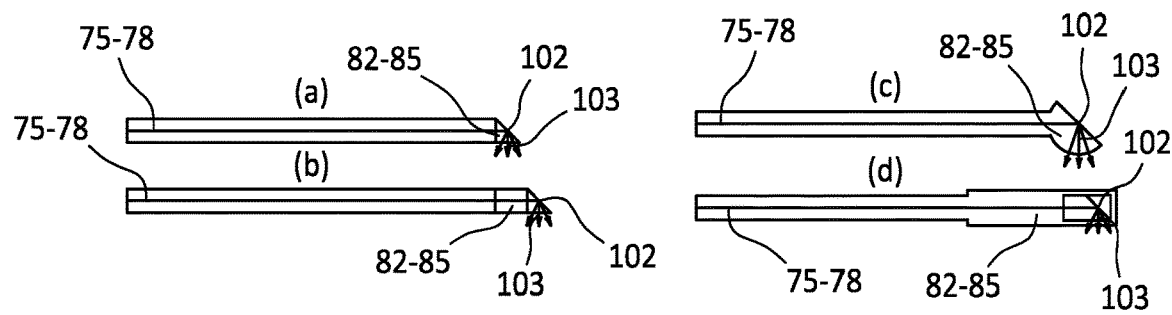
FIG. 18 is schematic representation of embodiments of light deflectors in accordance with the present disclosure.

Referring to FIG. 18 there is shown a number of different embodiments (a-d) for light deflectors 82-85 attached to optical fiber leads 75-78. Each of the light deflectors 82-85 includes a light reflective surface 102 positioned at an angle to the emitted light and a light transmissive portion 103 to allow the emitted light to exit the light deflector and produce the irradiance patterns disclosed above. Light reflective surface 102 can comprise any suitable efficient device or coating such as a gold coating. Transmissive portion 103 can comprise any optically transmissive device such as a window, a slot, a lens, a diffuser and the like.

Figure 19:
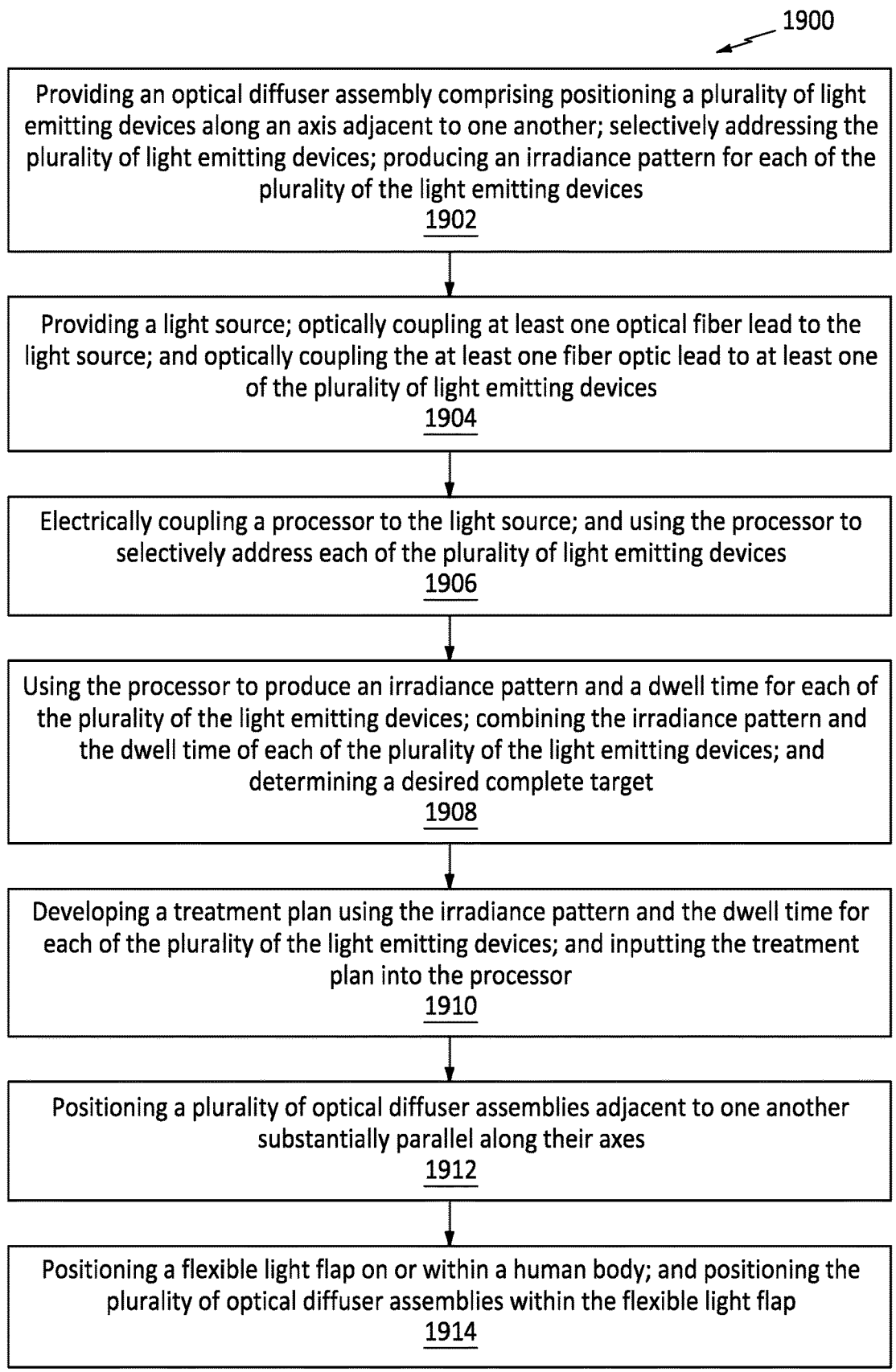
FIG. 19 is a flowchart of an example process 1900 using a configurable optical applicator in accordance with the present disclosure.

FIG. 19 is a flowchart of an example process 1900. In some implementations, one or more process blocks of FIG. 19 may be performed by a configurable optical applicator as disclosed herein above. As shown in FIG. 19, process 1900 may include providing an optical diffuser assembly having: positioning a plurality of light emitting devices along an axis adjacent to one another; selectively addressing the plurality of light emitting devices; producing an irradiance pattern for each of the plurality of the light emitting devices (block 1902). For example, the device may provide an optical diffuser assembly positioning a plurality of light emitting devices along an axis adjacent to one another, selectively addressing the plurality of light emitting devices and producing an irradiance pattern for each of the plurality of the light emitting devices, as described above.

Process 1900 may include additional implementations, such as any single implementation or any combination of implementations described below and/or in connection with one or more other processes described elsewhere herein. In a first implementation, process 1900 further includes providing a light source, optically coupling at least one optical fiber lead to the light source, and optically coupling the at least one fiber optic lead to at least one of the plurality of light emitting devices.

In a second implementation, alone or in combination with the first implementation, process 1900 further includes electrically coupling a processor to the light source and using the processor to selectively address each of the plurality of light emitting devices.

In a third implementation, alone or in combination with the first and second implementation, process 1900 further includes using the processor to produce an irradiance pattern and a dwell time for each of the plurality of the light emitting devices, combining the irradiance pattern and the dwell time of each of the plurality of the light emitting devices, and determining a desired complete target.

In a fourth implementation, alone or in combination with one or more of the first through third implementations, process 1900 further includes developing a treatment plan using the irradiance pattern and the dwell time for each of the plurality of the light emitting devices, and inputting the treatment plan into the processor.

In a fifth implementation, alone or in combination with one or more of the first through fourth implementations, process 1900 further includes delivering optical light to a target tissue, positioning a plurality of optical diffuser assemblies adjacent to one another substantially parallel along their axes.

In a sixth implementation, alone or in combination with one or more of the first through fifth implementations, process 1900 may include positioning a flexible light flap on or within a human body, and positioning the plurality of optical diffuser assemblies within the flexible light flap.

Although FIG. 19 shows example blocks of process 1900, in some implementations, process 1900 may include additional blocks, fewer blocks, different blocks, or differently arranged blocks than those depicted in FIG. 19. Additionally, or alternatively, two or more of the blocks of process 1900 may be performed in parallel.

It is an aspect of the present disclosure that the configurable optical applicators disclosed herein can be advantageously used and/or controlled by artificial intelligence techniques such as those disclosed in co-pending provisional U.S. patent application Ser. No. 62/994,404 filed 20 Mar. 2020 titled "OPTICAL APPLICATOR FEATURE OPTIMIZER", the disclosure of which is incorporated herein in its entirety. It is another aspect of the present disclosure that the configurable optical applicators disclosed herein can be advantageously used and/or controlled by artificial intelligence techniques such as those disclosed in co-pending provisional U.S. patent application Ser. No. 63/020,142 filed 5 May 2020 titled "AVERAGE POWER MODULATED OPTICAL APPLICATOR", the disclosure of which is incorporated herein in its entirety.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention.

Although the invention(s) is/are described herein with reference to specific embodiments, various modifications and changes can be made without departing from the scope of the present invention(s), as presently set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise the terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

While the foregoing is directed to embodiments of the present invention, other and further embodiments of the invention may be devised without departing from the basic scope thereof, and the scope thereof is determined by the claims that follow.

What is claimed is:

1. A method of delivering optical light to a target tissue comprising:
    providing an optical diffuser assembly comprising:
        providing an optically transmissive catheter having an axial length;
        fixedly positioning a plurality of light emitting devices within the optically transmissive catheter at a plurality of positions along the axial length adjacent to one another;
        selectively addressing the plurality of light emitting devices; and
        producing an irradiance pattern for each of the plurality of the light emitting devices at each of the plurality of positions;
    providing a light source;
    optically coupling the light source to the plurality of light emitting devices;
    electrically coupling a processor to the light source;
    using the processor to selectively address each of the plurality of light emitting devices;
    using the processor to produce an irradiance pattern and a dwell time for each of the plurality of the light emitting devices;
    combining the irradiance pattern and the dwell time of each of the plurality of the light emitting devices; and
    determining a desired complete target.

2. The method of delivering optical light to a target tissue of claim 1, wherein the plurality of light emitting devices comprises:
    an optical light diffuser having a first segment and a second segment positioned along the axis adjacent to one another; and
    the method further comprises:
    emitting light at a first wavelength from the first segment; and
    emitting light at a second wavelength from the second segment.

3. The method of delivering optical light to a target tissue of claim 2, further comprising:
    blocking light at the second wavelength using a first thin-film notch filter on at least a portion of the first segment; and
    blocking light at the first wavelength using a second thin-film notch filter on at least a portion of the second segment.

4. The method of delivering optical light to a target tissue of claim 3, wherein at least a portion of the first segment comprises a light reflective surface and at least a portion of the second segment comprises a light reflective surface.

5. A device for delivering optical light to a target tissue comprising:
    an optical diffuser assembly comprising:
    an optically transmissive catheter having an axial length;

a plurality of light emitting devices fixedly positioned along the axial length adjacent to one another;
a light source;
at least one optical fiber lead coupled to the light source and the at least one optical fiber lead coupled to at least one of the plurality of light emitting devices;
a processor electrically coupled to the light source;
the processor configured to selectively address each of the plurality of light emitting devices; and
the processor further configured to produce an irradiance pattern and a dwell time for each of the plurality of the light emitting devices and to combine the irradiance pattern and the dwell time of each of the plurality of the light emitting devices and to determine a desired complete target.

6. The device of claim 5, wherein the plurality of light emitting devices comprises:
an optical light diffuser having a first segment and a second segment positioned along the axis adjacent to one another; and
the device further comprises:
configured to emit emitting light at a first wavelength from the first segment; and
configured to emit emitting light at a second wavelength from the second segment.

7. The device of claim 6, further comprising:
a first thin-film notch filter positioned on at least a portion of the first segment configured to block blocking light at the second wavelength using a first thin-film notch filter on at least a portion of the first segment; and
a second thin-film notch filter positioned on at least a portion of the second segment configured to blocking light at the first wavelength using a second thin-film notch filter on at least a portion of the second segment.

8. The device of claim 7, wherein at least a portion of the first segment comprises a light reflective surface and at least a portion of the second segment comprises a light reflective surface.

* * * * *